(12) United States Patent
Didden et al.

(10) Patent No.: US 12,138,417 B2
(45) Date of Patent: Nov. 12, 2024

(54) WORKPIECE CARRIER FOR COMPONENTS OF DRUG DELIVERY DEVICES

(71) Applicant: Sanofi, Paris (FR)

(72) Inventors: Fabian Didden, Frankfurt am Main (DE); Brunhilde Gootz, Frankfurt am Main (DE); Frank Bien, Frankfurt am Main (DE); Markus Neumann, Frankfurt am Main (DE); Sebastian Tan, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/008,405

(22) PCT Filed: Jun. 23, 2021

(86) PCT No.: PCT/EP2021/067059
§ 371 (c)(1),
(2) Date: Dec. 5, 2022

(87) PCT Pub. No.: WO2021/259964
PCT Pub. Date: Dec. 30, 2021

(65) Prior Publication Data
US 2023/0201450 A1     Jun. 29, 2023

(30) Foreign Application Priority Data
Jun. 25, 2020     (EP) .................................... 20315318

(51) Int. Cl.
*A61M 5/00*     (2006.01)
(52) U.S. Cl.
CPC ................... *A61M 5/008* (2013.01)

(58) Field of Classification Search
CPC ............................... A61M 5/008; A61M 5/001
(Continued)

(56) References Cited

U.S. PATENT DOCUMENTS

| 3,643,812 A * | 2/1972 | Mander ...................... B01L 9/06 220/519 |
| 4,982,850 A * | 1/1991 | Mears .................... A61M 5/008 D24/227 |

(Continued)

FOREIGN PATENT DOCUMENTS

| DE | 102022004654 B3 * | 2/2024 | ............. G01B 11/14 |
| JP | 2007-106449 | 4/2007 | |

(Continued)

OTHER PUBLICATIONS

International Preliminary Report on Patentability in International Appln. No. PCT/EP2021/067059, mailed on Jan. 5, 2023, 8 pages.

(Continued)

*Primary Examiner* — Jennifer E. Novosad
(74) *Attorney, Agent, or Firm* — Bond, Schoeneck & King, PLLC (57) ABSTRACT

A workpiece carrier for transporting and/or storing components of a drug delivery device. The workpiece carrier includes a body including a planar-shaped bottom area. The planar-shaped bottom area includes an upper side and a bottom side opposite to the upper side. The bottom area includes a number of longitudinally extending hollow protuberances protruding from the bottom side and forming longitudinally extending cavities in the upper side. A longitudinal end of at least one of the protuberances or cavities faces away from the bottom side comprises an aperture.

22 Claims, 5 Drawing Sheets

(58) Field of Classification Search
USPC .................. 211/85.13, 85.18; 206/364, 562; 422/300
See application file for complete search history.

(56) References Cited

U.S. PATENT DOCUMENTS

| | | | | |
|---|---|---|---|---|
| 5,129,886 | A * | 7/1992 | Sincock | A61M 5/008 604/263 |
| 5,996,818 | A * | 12/1999 | Boje | A47F 7/0028 422/549 |
| 7,169,361 | B2 * | 1/2007 | Arnold, Jr. | G01N 35/10 422/526 |
| 8,196,741 | B2 * | 6/2012 | Finke | A61M 5/008 211/74 |
| 8,485,357 | B2 * | 7/2013 | Song | B01L 9/00 211/74 |
| 8,505,723 | B2 * | 8/2013 | Clark | B65D 5/503 206/443 |
| 8,561,828 | B2 * | 10/2013 | Krauss | A61J 1/16 220/507 |
| 8,852,158 | B1 * | 10/2014 | Schaffer | A61M 5/008 604/263 |
| 8,939,288 | B2 * | 1/2015 | Gagnieux | B65D 25/108 206/439 |
| 9,408,965 | B2 * | 8/2016 | Christensen | B65D 25/108 |
| 9,468,711 | B2 * | 10/2016 | Iwase | A61M 5/008 |
| 9,586,722 | B2 * | 3/2017 | Josef | B65D 21/0216 |
| 9,718,583 | B2 * | 8/2017 | Nicoletti | B65D 65/02 |
| 9,783,328 | B2 * | 10/2017 | Liversidge | B65D 25/34 |
| 10,143,793 | B2 * | 12/2018 | Gagnieux | A61M 5/008 |
| 10,207,832 | B2 * | 2/2019 | Narvekar | A61J 1/1412 |
| 10,703,539 | B2 * | 7/2020 | Deutschle | B65D 25/108 |
| 11,559,802 | B2 * | 1/2023 | Cote | B01L 3/5025 |
| 2006/0016156 | A1 * | 1/2006 | Bush | B65D 77/0446 53/469 |
| 2006/0266719 | A1 * | 11/2006 | Knight | G01N 35/025 211/74 |
| 2009/0065458 | A1 * | 3/2009 | Murray | B01L 9/06 211/85.18 |
| 2012/0103861 | A1 * | 5/2012 | Song | A61B 50/33 206/563 |
| 2013/0048531 | A1 * | 2/2013 | Nicoletti | A61M 5/008 206/557 |
| 2013/0186793 | A1 * | 7/2013 | Gagnieux | A61M 5/008 206/364 |
| 2014/0353190 | A1 * | 12/2014 | Okihara | B65B 55/10 206/370 |
| 2019/0298610 | A1 * | 10/2019 | Komann | A61M 5/008 |
| 2020/0130894 | A1 * | 4/2020 | Kusogullari | B65D 25/108 |
| 2023/0025555 | A1 * | 1/2023 | Wells | A61M 5/008 |
| 2023/0201450 | A1 * | 6/2023 | Didden | A61M 5/001 211/85.13 |

FOREIGN PATENT DOCUMENTS

| | | | | |
|---|---|---|---|---|
| WO | WO-2011007194 A1 * | 1/2011 | ............ | A61B 50/33 |
| WO | WO 2021/259964 | 12/2021 | | |
| WO | WO-2021259964 A1 * | 12/2021 | ............ | A61M 5/001 |

OTHER PUBLICATIONS

International Search Report and Written Opinion in International Appln. No. PCT/EP2021/067059, mailed on Jul. 27, 2021, 9 pages.

* cited by examiner

WORKPIECE CARRIER FOR COMPONENTS OF DRUG DELIVERY DEVICES

CROSS-REFERENCE TO RELATED APPLICATIONS

The present application is the national stage entry of International Patent Application No. PCT/EP2021/067059, filed on Jun. 23, 2021, and claims priority to Application No. EP 20315318.4, filed on Jun. 25, 2020, the disclosures of which are incorporated herein by reference.

TECHNICAL FIELD

The present disclosure relates to a workpiece carrier for transporting and/or storing components, in particular components or sub-assemblies of drug delivery devices, such as injection devices, e.g. implemented as pen-type injectors. The disclosure further relates to a workpiece carrier assembly comprising at least a first and a second workpiece carrier stacked on top of each other or arranged next to each other.

BACKGROUND

Drug delivery devices, such as handheld injection devices, allowing for multiple dosing of a required dosage of a liquid medicament or liquid medicinal product and further providing administration of such liquid medicament or drug to a patient, are as such known in the prior art. Generally, such devices have substantially the same purpose as that of an ordinary syringe.

Drug delivery devices of this kind have to meet a number of user specific requirements. For instance, in case of those with diabetes, many users will be physically infirm and may also have impaired vision. Therefore, these devices need to be robust in construction, yet easy to use, both in terms of the manipulation of the parts and understanding by a user of its operation. Further, the dose setting and dose delivery should be easy and unambiguous and where the device is to be disposable rather than reusable, the device should be inexpensive to manufacture and easy to dispose.

Typically, a medicament to be delivered by such drug delivery or injection devices is provided in a cartridge having a moveable piston or stopper mechanically interacting with a piston rod of a drive mechanism of the drug delivery device. By applying thrust to the piston in a longitudinal distal direction, a certain amount of the medicament is expelled from the cartridge.

Manufacturing and final assemblage of such drug delivery devices is typically implemented in a mass-production process. Typically, various components of the drug delivery device are manufactured and/or even pre-configured by various suppliers. Some suppliers may provide a cartridge with the medicament. Other suppliers may provide the various mechanical components of the injection device and/or of its drive mechanism.

For a fully automated assembly of such drug delivery or injection devices the numerous components the device is made of have to be provided to an automated assembly line in a well-defined order. For instance, with disposable drug delivery or injection devices, the cartridge containing the medicament has to be positioned in a dedicated housing component of the injection device, also denoted as cartridge holder. In a final step of assembly the pre-assembly comprising the cartridge holder with the cartridge located therein is attached to a housing or body of the injection device.

Since the assembly or final assembly of such drug delivery devices has to be conducted almost entirely automatically, the numerous components of the drug delivery device or a sub-assembly of at least two components of the drug delivery device have to be provided in a well-defined and ordered way.

Insofar, the components of a drug delivery device or injection device have to be correctly oriented and arranged on a mechanical support structure, e.g. on a workpiece carrier. Such workpiece carriers may provide storage space and/or support space for a large number of drug delivery devices or injection devices.

Here, optimization of transportation and handling of a large number of components for injection devices or drug delivery devices in terms of required storage or shipping space is a persistent aim for reducing costs of manufacture and logistics in mass production or masse assembly processes. Moreover, such workpiece carriers should be lightweight and should provide a high precision assembly of drug delivery devices.

With some drug delivery devices or injection devices the assembly has to take place in a clean or even sterile environment that fulfils the demands of a predefined cleanroom class. In view of this, the workpiece carriers should allow and support an easy and effective cleaning. In addition, workpiece carriers stacked on top of each other and/or arranged next to each other during transportation and/or storage should remain in a stable configuration to allow and to support a well-defined automated handling.

SUMMARY

In one aspect there is provided a workpiece carrier for transporting and/or storing components of a drug delivery device. The workpiece carrier comprises a body. The body comprises a planar-shaped bottom area. The planar-shaped bottom area comprises an upper side and a bottom side opposite to the upper side. The bottom area comprises a number of longitudinally extending hollow protuberances protruding from the bottom side and forming longitudinally extending cavities in the upper side. Particularly, the protuberances are inversely shaped to the respective cavities. The cavities and protuberances comprise a comparatively thin sidewall. Insofar, an outer shape or cross-section of the protuberances directly matches and corresponds to an inner shape or cross-section of the respective cavities.

In particular and with some examples an outside surface of at least one of the protuberances matches in size and shape with an inside surface of at least one of the cavities. Typically, the outside surface of each one of the protuberances matches in size and shape with an inside surface of each one of the cavities. This allows and enables a nested or convoluted arrangement of protuberances and cavities. In a stacked configuration of at least two identically shaped workpiece carriers according to the present disclosure another workpiece carrier, i.e. a second workpiece carrier, may be stacked and/or arranged on top of the workpiece carrier, i.e. a first workpiece carrier. Here the protuberances protruding from the bottom side of the second workpiece carrier are allowed to enter into the cavities provided in the upper side of the first workpiece carrier. In this way a rather compact and stacked arrangement of numerous workpiece carriers can be provided. The cavities are particularly shaped to receive at least one or numerous components of a drug delivery device. With some examples the cavities are shaped to receive at least one longitudinally extended component of a drug delivery device in an upright way. Typically, the cavities are shaped to receive a longitudinally extending sleeve shape component of a drug delivery device, such as a longitudinally and tubular shaped housing component, a tubular shaped cartridge and/or a tubular shaped number sleeve or gauge element of the drive mechanism of the drug delivery device. Typically, the workpiece carrier and the cavities are configured to receive or to accommodate components of a pen-type injector.

With some examples of the workpiece carrier a longitudinal end of at least one of the protuberances or cavities that faces away from the bottom side comprises an aperture. The aperture may be implemented as an open longitudinal end of the respective cavity or protuberance. Typically, all protuberances or cavities of the body are provided with an aperture. The aperture may be implemented as a bottom aperture. The aperture provides an open end of the respective protuberances or cavities. In this way a cleaning detergent used for cleaning of the workpiece carrier is allowed to easily drain from the cavities. Cleaning and drying of workpiece carriers can be therefore simplified and facilitated. An open longitudinal end of the protuberances or cavities is further beneficial to prevent aggregation of impurities, such as dust or humidity.

According to a further or alternative example the body of the workpiece carrier is a one-piece injection molded plastic body. An injection molded plastic body is of particular benefit to provide a comparatively small dimensional tolerances and a high degree of size accuracy. This is of benefit for stacking numerous workpiece carriers onto each other. Moreover a high degree of size accuracy is also beneficial for a precise, e.g. robot-controlled insertion of components of the drug delivery device into the cavities as well as for a well-defined withdrawal of such components from the respective cavities.

Injection molded workpiece carriers, typically implemented as transportation and/or storage trays for drug delivery devices or injection devices are dimensionally more stable compared to workpiece carriers manufactured by deep drawing. Injection molded workpiece carriers further enable and support a repeated use of workpiece carriers and to establish a closed circuit of using, cleaning and reusing of workpiece carriers multiple times.

According to a further or alternative example the body comprises a number of depressions in the upper side of the bottom area. Here, the depressions and the cavities are adjacently arranged in an alternating order along a first direction. Typically, the depressions are shaped and sized in the upper side of the bottom area to receive or to engage with the longitudinal end of the protuberances of another workpiece carrier stacked on the workpiece carrier.

Typically, each depression may provide a support platform for the lower longitudinal end of another workpiece carrier stacked on or arranged on the respective workpiece carrier. Typically, the depth of the depressions is much smaller than the depth of the cavities on the upper side of the planar-shaped bottom average of the workpiece carrier.

The depressions are particularly shaped to receive the longitudinal end of the protuberances in a self-centering way. The mutually corresponding shapes of depressions and of the longitudinal ends of the protuberances provide a kind of a mechanical engagement when a second workpiece carrier is arranged on top of a first workpiece carrier. In this way, a stack of workpiece carriers and hence a workpiece carrier assembly comprising at least a first and a second workpiece carrier stacked on top of each other can be provided in a mechanically stable manner. A second workpiece carrier can be precisely aligned with regards to its position in the plane of the planar-shaped bottom area when the protuberances or protrusions of the second workpiece carrier are arranged in the depressions of the first workpiece carrier.

Typically, the geometric shape, e.g. the transverse cross-section of the depressions matches and/or corresponds to the geometric shape of the longitudinal end of the protuberances. With some examples the depressions may comprise a somewhat circular structure. Here, the longitudinal ends of the protuberances may comprise a correspondingly shaped circular structure. With other examples, the longitudinal end of the protuberances comprises a somewhat rectangular or polygonal structure also matching with the circular structure of the respective depressions.

According to another example the body comprises a row of cavities extending along a second direction. Additionally or alternatively, the body comprises a row of depressions extending along the second direction. Typically, the second direction extends perpendicular to the first direction. The first direction and the second direction typically coincide with or lie in the plane of the planar-shaped bottom area.

The row of cavities extending along the second direction comprises at least a first cavity and a second cavity. The second cavity is arranged next to the first cavity along the second direction. There may be provided also a row of depressions. The row of depressions may be offset to the row of the cavities along the first direction. Here, a first depression of a first row of depressions may be located adjacent to a first cavity of a first row of cavities. Likewise, a second depression of the first row of depressions may be located adjacent to a second cavity of the first row of cavities. The first row of depressions is located next to the first row of cavities but is located offset from the first row of cavities along the first direction.

The row of depressions and the row of cavities may extend parallel to each other. The distance of cavities in a row of cavities may be substantially equal to the distance between the depressions in a row of depressions. Here, the distance is measured between a center region of the cavities or depressions, respectively.

With some examples, there is provided a two-dimensional array of cavities and depressions. Along the first direction there might be provided an alternating arrangement of cavities and depressions. Along the second direction there might be provided rows of cavities and row of depressions, wherein the elongation of the rows is parallel to the second direction.

Typically, there will be an equal number of cavities and depressions. They will be also an equal number of rows of cavities and rows of depressions.

With some examples there is provided a first row of cavities extending along the second direction. Along the first direction and adjacent to the first row of cavities there is provided a first row of depressions.

Adjacent to the first row of depressions along the first direction there may be provided a second row of cavities. Then there may follow a second row of depressions and so on. As seen along the first direction there will be provided alternating rows of cavities and depressions.

Typically and with a further example, the workpiece carrier, at least it's planar-shaped bottom area comprises a mirror symmetry. A line of symmetry may extend along the first direction. In this way, and end section of the body or of its planar-shaped bottom area as seen along the second direction is symmetric to an oppositely located second end of the body or of its planar-shaped bottom area as seen in the second direction.

The mirror symmetry provides and enables two configurations for stacking workpiece carriers on top of each other. In a first configuration identical workpiece carriers may be stacked on top of each other in an identical orientation. In a second configuration a second workpiece carrier arranged on top of a first workpiece carrier may be rotated by about 180° compared to the first workpiece carrier. Then, a third workpiece carrier to be stacked on top of the second workpiece carrier may be oriented identical to the first workpiece carrier. A fourth workpiece carrier to be stacked on top of the third workpiece carrier may be oriented identical to the second workpiece carrier and so on. Every second workpiece carrier in a stack of workpiece carriers is in the same orientation. Workpiece carriers located directly adjacent on top of each other in a stack of workpiece carriers are oriented or slipped over by 180° compared to the adjacently located workpiece carrier.

In a first configuration of a workpiece carrier assembly, wherein a second workpiece carrier is stacked on top of a first workpiece carrier, the protuberances of the second workpiece carrier may enter the cavities of the first workpiece carrier from above. In the second configuration, hence when the second workpiece carrier is rotated by about 180° with regard to an axis of rotation extending substantially parallel to a surface normal in a surface center section of the planar-shaped bottom area, the protuberances of the second workpiece carrier substantially align with the depressions of the first workpiece carrier.

In the second configuration the stack height of a workpiece carrier assembly may be larger than a respective stack height of a workpiece carrier assembly in the first configuration. Here, and since the protuberances abut with the depressions the protuberances of the second workpiece carrier they do not sink into the cavities of the first workpiece carrier. Interstices on the bottom side of the bottom area located between adjacently located protuberances of a second workpiece carrier are aligned with the cavities of the first workpiece carrier and therefore provide room for an upright orientation and accommodation of elongated or longitudinally shaped components of a drug delivery device. Here, at least portions of longitudinally extending component of the drug delivery device inserted into a cavity of the first workpiece carrier may protrude out of the cavity and into the interstices between protuberances of the second workpiece carrier.

According to another example the depressions comprise a concave shaped cross-section. A concave shaped cross-section is beneficial to provide a self-centering of first and second workpiece carriers stacked on top of each other in the second configuration. Here, the concave shaped depressions of the first workpiece carrier provide a well-defined lateral alignment of the protuberances of the second workpiece carrier when stacked on top of the first workpiece carrier.

In this way, a rather stable and self-supporting arrangement of a large number of protuberances of the second workpiece carrier supported by a respective number of depressions of the first workpiece carrier can be provided. Typically, in the second configuration of a workpiece carrier assembly comprising a first second workpiece carrier stacked or arranged on top of a first workpiece carrier each or almost each protuberance of the second workpiece carrier can be directly mechanically supported by a correspondingly shaped depression of the first workpiece carrier. In this way, a rather stable mechanical arrangement of numerous workpiece carriers on top of each other can be provided.

According to another example the depressions comprise a hole or aperture extending through the bottom area. Typically, the hole or aperture is located in a central region of the depression. When the depression comprises a circular shape or symmetry the hole is located in a radial center region. Furthermore, when the depression comprises a concave structure the whole is located in a bottom region and/or center region of the concave structure. It is located at a deepest location inside the depression. The hole itself may also comprise a circular structure.

The hole or aperture in the depression provides and supports drainage of a liquid cleaning agent. Moreover, when multiple trays or workpiece carriers are stacked on top of each other in accordance to the second configuration the aperture of a protuberance of a second workpiece carrier on top of a first workpiece carrier may align in vertical direction with the hole or aperture of the respective depression of the first workpiece carrier. In this way, a liquid agent draining through the aperture of a protuberance of the second workpiece carrier may also flow through the hole of a depression of the first workpiece carrier located underneath.

According to another example the body of the workpiece carrier comprises a side wall. The sidewall protrudes from the upper side of the planar-shaped bottom area. The sidewall surrounds the planar-shaped bottom area. Typically, the sidewall and the bottom area are integrally formed. Both, the sidewall and the bottom area can be formed by way of an injection molding of a suitable plastic material, such as a thermoplastic material, e.g. acrylonitrile butadiene styrene (ABS), polypropylene (PP) or polystyrene (PS), e.g. a high impact polystyrene (HIPS).

The sidewall may surround and enclose the planar-shaped bottom area. The sidewall may form a closed frame structure. The sidewall may also provide and support for stacking of numerous workpiece carriers on top of each other. For instance, in a first configuration of a workpiece carrier assembly wherein a second workpiece carrier is stacked on top of a first workpiece carrier, an inside surface of a sidewall of the first workpiece carrier may engage with an outside surface of a sidewall of the second workpiece carrier. In this way a kind of a nested or convoluted arrangement of first and second workpiece carriers can be provided. Also in the second configuration of such a workpiece carrier assembly the outside surface of the sidewall of the second workpiece carrier may be located inside the inside surface of the sidewall of the first workpiece carrier.

In the second configuration it may not be necessary that the outside surface of the sidewall of the second workpiece carrier snugly engages the inside surface of the sidewall of the first workpiece carrier. There may be provided a gap or a distance between the inside and outside surfaces of the sidewalls of first and second workpiece carriers when in the second configuration. Nevertheless, the upwardly protruding sidewall of the first workpiece carrier provides at least a visual and/or mechanical guiding functionality for arranging the second workpiece carrier on top of the first workpiece carrier in the second configuration.

The upwardly extending sidewall of the workpiece carrier provides an enhanced mechanical stability to the body. The body may be stiffened by the side wall and may therefore provide a rather stable mechanical support for the components of the drug delivery device.

According to a further example the workpiece carrier comprises at least one strut extending inwardly from an inside surface of the sidewall and extending upwardly from the upper side of the planar-shaped bottom area. The at least one strut interconnects the sidewall and the bottom area. Typically, the sidewall, the bottom area and the strut are integrally formed. The strut may comprise a planar triangular shaped structure. Here, a first leg of the triangular shaped strut may align along the inside surface of the sidewall. A second leg of the triangular-shaped strut may extend along the upper side of the planar-shaped bottom area. A hypotenuse of the at least one strut provides and forms an inwardly protruding edge of the strut.

Typically, the at least one strut narrows towards the upper end of the sidewall, away from the bottom area. The at least one strut provides a beveled section in the corner of the sidewall and the upper side of the bottom area. Typically, there are provided numerous struts distributed along the outer circumference of the bottom area and the inside surface of the side wall.

The inwardly extending struts are of particular benefit for an injection molded plastic body. Such struts serve to prevent formation of sink marks. Moreover, the at least one strut or the numerous struts serve to maintain the dimensions of the injection molded plastic body of the process of injection molding and when subject to cooling from a melting temperature of the plastic components to ambient temperature.

According to another aspect the at least one strut may provide a stop feature for arranging first and second workpiece carriers in a nested configuration, namely when the second workpiece carrier is stacked on top of the first workpiece carrier in the first configuration. Here, the beveled strut or numerous struts of the first workpiece carrier may provide a stop for an outer edge of the planar-shaped bottom area of a body of the second workpiece carrier when in the first configuration.

The beveled shape of the strut or strut may also contribute to prevent a mutual jamming of first and second workpiece carriers arranged in the first configuration. The beveled shape of the at least one strut or of numerous struts provides a punctual abutment with the bottom area of the workpiece carrier stacked thereon.

According to another example the sidewall comprises at least one longitudinally extending rib protruding from an outside surface of the sidewall. Typically, the longitudinally extending rib extends substantially parallel to a surface normal of the planar-shaped bottom area. The longitudinally extending rib or numerous longitudinally extending ribs may provide enhanced stability for the sidewall. They may further provide a well-defined gripping structure for an automated gripping of the workpiece carrier, e.g. by a robot arm.

With some examples an upper end of the sidewall comprises a flange. The flange typically extends outwardly from an outside surface of the sidewall. The flange provides a well-defined gripping of the workpiece carrier from above. Typically, the longitudinally extending rib or ribs and the flange comprise the same or comparable protrusions from the outside surface of the side wall. An upper end of the longitudinally extending rib may adjoin or may be located adjacent to a lower edge of the outwardly protruding flange. An outwardly facing edge of the longitudinally extending rib may flush with the flange.

According to another example the at least one longitudinally extending rib comprises a lower end located at a predefined distance from the bottom area. The outwardly protruding rib and its lower end may be configured to abut in vertical direction onto an upper end of a sidewall of a workpiece carrier located underneath. So with a workpiece carrier assembly comprising a first workpiece carrier and a second workpiece carrier on top of the first workpiece carrier the lower end of the at least one longitudinally extending rib of the second workpiece carrier may abut an upper end of a sidewall, e.g. a flange of the sidewall of the first workpiece carrier.

This mutual abutment may be particularly obtained when the first and second workpiece carriers are arranged in the first configuration, i.e. when the orientation of the first workpiece carrier is somewhat identical to the orientation of the second workpiece carrier.

The longitudinally extending rib or numerous longitudinally extending ribs distributed along the outer circumference of the sidewall provides and enables an optimized demolding when the workpiece carrier is implemented as an injection molded plastic body. The longitudinally extending rib or longitudinally extending ribs may be rather straight and linearly shaped, which enables a respective demolding.

According to a further example the sidewall of the workpiece carrier comprises a first crossbeam extending along a first angle on an outside surface of the first sidewall portion of the sidewall and protruding outwardly from the first sidewall portion. The degree protrusion of the first crossbeam to the outside direction may be equal to or substantially identical to the degree of protrusion of the longitudinally extending rib and/or the protrusion of the flange of the sidewall. The crossbeam is located at a particular position on a first sidewall portion that corresponds to a second position of a second sidewall portion located opposite to the first sidewall portion.

The crossbeam particularly serves to prevent a lateral intrusion, nesting or convolution of workpiece carriers arranged next to each other. Typically, and with a first and a second workpiece carrier being arranged next to each other the crossbeam of the first workpiece carrier may engage or abut with a complementary-shaped crossbeam of the second workpiece carrier.

Here, the first and the second crossbeams can extend at different angles so that the crossbeams punctually abut in a lateral direction. Generally, and with the first crossbeam being arranged or oriented at a non-zero angle with regard to the extension of the longitudinally extending rib the first crossbeam of a first workpiece carrier may get in abutment to a longitudinally extending rib of a second workpiece carrier arranged adjacently to the first workpiece carrier. In this way and by making use of a tilted or slanted crossbeam protruding from the outside surface of the sidewall, a laterally nested arrangement of workpiece carriers arranged next to each other can be effectively prevented. Otherwise, protruding structures on the outside surface of a first and a second workpiece carrier extending parallel to each other, such as a flange or longitudinally extending ribs, may at least partially intersect each other. This may be detrimental for the individual handling of a single workpiece carrier.

Such a mutual intersection of adjacently arranged workpiece carriers can be effectively prevented by providing at least a first crossbeam extending at a predefined, i.e. non-zero angle with regard to the extension of the surface normal of the bottom area and/or with regard to the elongation of ribs on the outside surface of the sidewall. Typically, there are provided numerous cross beams along the outer circumference of the side wall.

Typically and with some examples, the workpiece carrier comprises a rectangular shaped bottom area and a correspondingly shaped somewhat rectangular side wall. A rectangular or even quadratic workpiece carrier provides and enables a well-defined and space-saving arrangement of numerous workpiece carriers next to each other. Typically, each one of the oppositely located outside surfaces of the sidewall can be provided at least with a first crossbeam. In this way, a nested and inadvertent sliding of first and second workpiece carriers at least partially into each other when arranged next to each other can be effectively avoided.

According to a further example, the rectangular structure of the sidewall may comprise or inner edges of the sidewall. Here, the inner edges may be rounded inner edges or corners between circumferentially adjacently located sidewall portions. The corner sections may comprise a rounded or concave shaped profile. This is of particular benefit for the molding process of an injection molded workpiece carrier.

According to another example the sidewall comprises at least one of a longitudinally extending rib and a second crossbeam extending along a second predefined angle on an outside surface of a second sidewall portion of the sidewall opposite to the first sidewall portion and protruding outwardly from the second sidewall portions. Here it is particularly preferred, that the second crossbeam or the longitudinally extending rib extend at an angle that is different to the first angle of the first crossbeam when first and second workpiece carriers are arranged next to each other. In such a configuration, the first crossbeam of the first workpiece carrier is located opposite and adjacent to at least one of the longitudinally extending rib and a second crossbeam of a second workpiece carrier.

Typically, the first crossbeam and one of the longitudinally extending rib and the second crossbeam are located directly opposite to each other on mutually opposite portions of the sidewall.

According to another example the first crossbeam and/or the second crossbeam may extend between or adjoin adjacently located longitudinally extending ribs on the outside surface of the sidewall. In this way the respective crossbeams may provide a further stiffening of the sidewall.

According to another example the sidewall comprises a lower sidewall section and an upper side wall section. The lower sidewall section adjoins the upper side of the bottom area and the upper side wall section adjoins the lower sidewall section via a stepped section. Accordingly, the stepped section is located between the lower side wall section and the upper sidewall section.

The cross-section or diameter of the upper side wall section may be slightly larger than the diameter or cross-section of the lower side wall section. Typically, the stepped section located between the upper side wall section and the lower sidewall section provides an outwardly protruding step as seen from the lower side wall section towards the upper sidewall section. The stepped section may provide an abutment for another workpiece carrier stacked on top of the workpiece carrier.

The stepped section may provide a well-defined stacking of a number of workpiece carriers on top of each other. Here, the stepped section of a first workpiece carrier may provide a support for an outside edge and/or lower edge of a planar-shaped bottom area of a second workpiece carrier stacked on top of the first workpiece carrier.

According to another example the cavities of the body of the workpiece carrier comprise an upper portion and a lower portion. The upper portion adjoins the bottom area and the lower portion adjoins of constitutes the longitudinal end of the cavity. Here, an inner diameter or cross-section of the lower portion is smaller than an inner diameter or cross-section of the upper portion. In other words, the cavity may comprise a tapered structure towards the longitudinal end facing away from the bottom side of the bottom area of the body. Such a tapered structure is beneficial for demolding of an injection molded workpiece carrier.

Additionally or alternatively, the lower portion of the cavity may form a stepped down longitudinal extension of the upper portion of the cavity. The lower portion may be shaped and configured to receive a particular or a dedicated component of the drug delivery device or injection device.

According to another example the upper portion of the cavity comprises a cross section and/or a cross-sectional shape that distinguishes from a cross-section and/or from a cross-sectional shape of the lower portion of the cavity. With some examples the upper portion may comprise a circular shaped cross-section and the bottom portion may comprise a semicircular shaped cross-section. In particular, the shape and/or an inner cross-section of the bottom portion may be particularly adapted and/or configured to receive a complementary shaped component of the drug delivery device.

According to another example of the workpiece carrier the upper portion of the cavity comprises a longitudinally extending separation wall dividing the upper portion at least into a first compartment and a second compartment. The separation wall may extend along or flush with an outside or inside wall of the lower portion of the workpiece carrier. Here, e.g. the first compartment separated by the separation wall may extend longitudinally into the bottom portion of the cavity. The second compartment may not extend into the lower portion of the cavity. Rather, the second compartment may be terminated in longitudinal direction by a bottom section coinciding with the lower end of the upper portion of the cavity.

With some examples there may be provided even two separation walls dividing the upper portion of the cavity into a first compartment, a second compartment and a third compartment. Here, each compartment may be dedicated or configured for receiving and/or accommodating a particular component of the drug delivery device. With some examples the separation wall may be T-shaped. Here, the first compartment may extend longitudinally from the upper portion into the lower portion of the cavity. Second and third compartments may be both located in the upper portion.

A T-shaped separation wall or numerous separation walls may provide a symmetry breaking feature for the cavity. In this way, only a longitudinally extending component that comprises a cross-section matching with the cross-section of that compartment of the cavity extending from the upper portion into the lower portion can be arranged and inserted into the cavity in a particular orientation or configuration that is demanded by the automatic assembly line.

Another aspect the disclosure further relates to a workpiece carrier assembly. The workpiece carrier assembly comprises a first workpiece carrier as described above and a second workpiece carrier as described above. The first and the second workpiece carriers being stackable onto each other in a first configuration and in a second configuration. When in the first configuration the second workpiece carrier is arranged on the first workpiece carrier in a first orientation which is identical to the orientation of the first workpiece carrier. When in the second configuration the second workpiece carrier is arranged on the first workpiece carrier in a second orientation. In this second orientation the second workpiece carrier is rotated by 180° compared to the first orientation.

In the following, the first orientation may be denoted as an initial orientation and the second orientation may be denoted as an inverted orientation. For transferring the workpiece carrier from the first orientation into the second orientation and hence for inverting the workpiece carrier it is intended to rotate the first workpiece carrier with respect to an axis of rotation, wherein the axis of rotation extends substantially parallel to a surface normal of the planar-shaped bottom area. Moreover, and with a rectangularly shaped workpiece carrier the axis of rotation is located in a geometric centerpoint of the bottom area.

The centerpoint may substantially coincide with an intersection of imaginary lines extending between middle sections of mutually oppositely located sidewall portions of the sidewall. Practically, and when transferring the second workpiece carrier from the first orientation into the second configuration first and third oppositely located sidewall portions as well as second and fourth oppositely located sidewall portions change position.

Generally, the scope of the present disclosure is defined by the content of the claims. The injection device is not limited to specific embodiments or examples but comprises any combination of elements of different embodiments or examples. Insofar, the present disclosure covers any combination of claims and any technically feasible combination of the features disclosed in connection with different examples or embodiments.

In the present context the term 'distal' or 'distal end' relates to an end of the injection device that faces towards an injection site of a person or of an animal. The term 'proximal' or 'proximal end' relates to an opposite end of the injection device, which is furthest away from an injection site of a person or of an animal.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

It will be further apparent to those skilled in the art that various modifications and variations can be made to the present disclosure without departing from the scope of the disclosure. Further, it is to be noted, that any reference numerals used in the appended claims are not to be construed as limiting the scope of the disclosure.

BRIEF DESCRIPTION OF THE FIGURES

In the following, examples of a workpiece carrier and a workpiece carrier assembly will be described in greater detail by making reference to the drawings, in which.

DETAILED DESCRIPTION

In FIGS. 1-13 there is illustrated a workpiece carrier 10 for transporting and/or storing components 60 of a drug delivery device 1. The workpiece carrier 10 comprises a body 11. The body 11 comprises a substantially planar-shaped bottom area 12. The bottom area 12 comprises an upper side 13 as seen and illustrated in FIG. 1 and an oppositely located bottom side 15. In the upper side 13 there are provided numerous cavities 14, 16, 18. The cavities 14, 16, 18 form protuberances 54 protruding from the bottom side 15. Typically, the protuberances 54 comprises a sidewall 51. An inside surface of the sidewall 51 of the protuberances 54 define and confine the respective cavity 14, 16, 18.

Figures 14, 15:
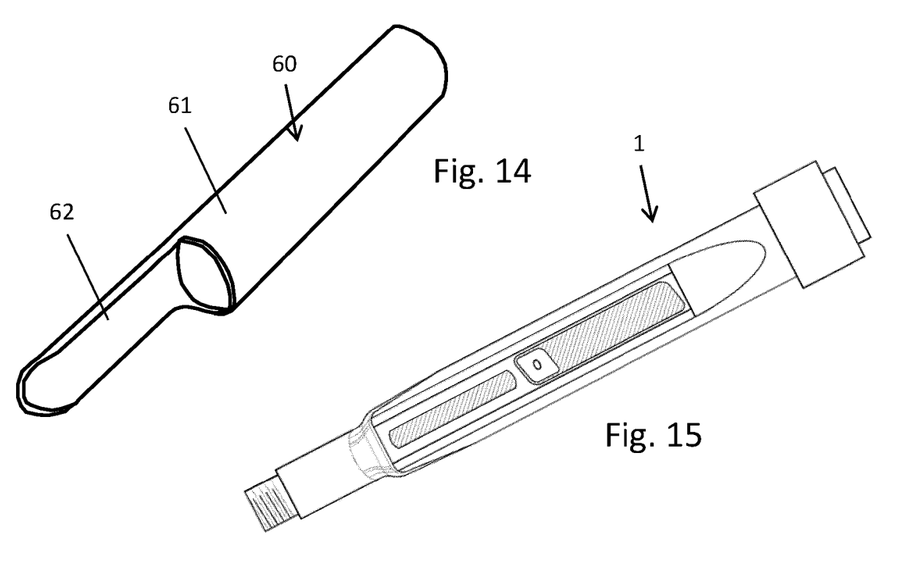
FIG. 14 shows an exemplary component 60 of a drug delivery device.
FIG. 15 shows an example of a drug delivery device having numerous components configured to become stored or transported with a workpiece carrier.

The cavities 14, 16, 18 are configured to receive or to accommodate at least an elongated component 60 of a drug delivery device 1 as illustrated in FIGS. 14 and 15. The drug delivery device 1 may be a handheld injection device, e.g. a pen-type injector. The cavities 14, 16, 18 are shaped in accordance to the component 60. As illustrated e.g. in FIG. 5 the cavities 14, 16, 18 comprise a somewhat circular symmetric shape at least in an upper part 28 adjoining the planar-shaped bottom area 12.

Figure 1:
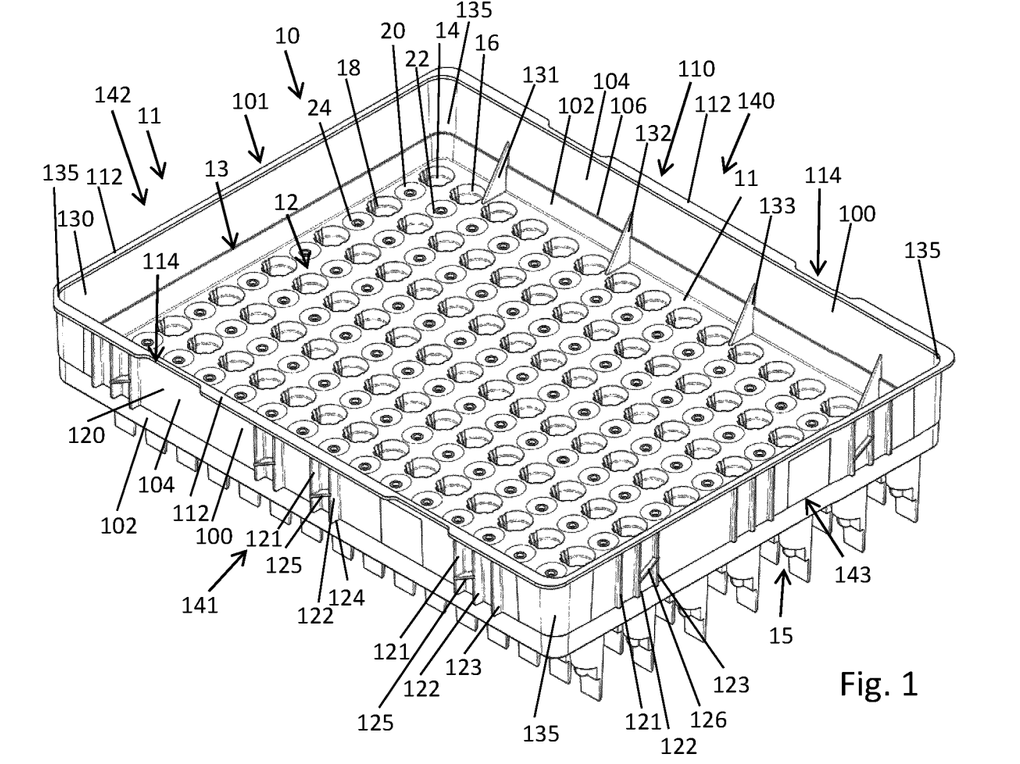
FIG. 1 shows a perspective illustration of an example of a workpiece carrier for transporting and/or storing components of a drug delivery device.
Figure 5:
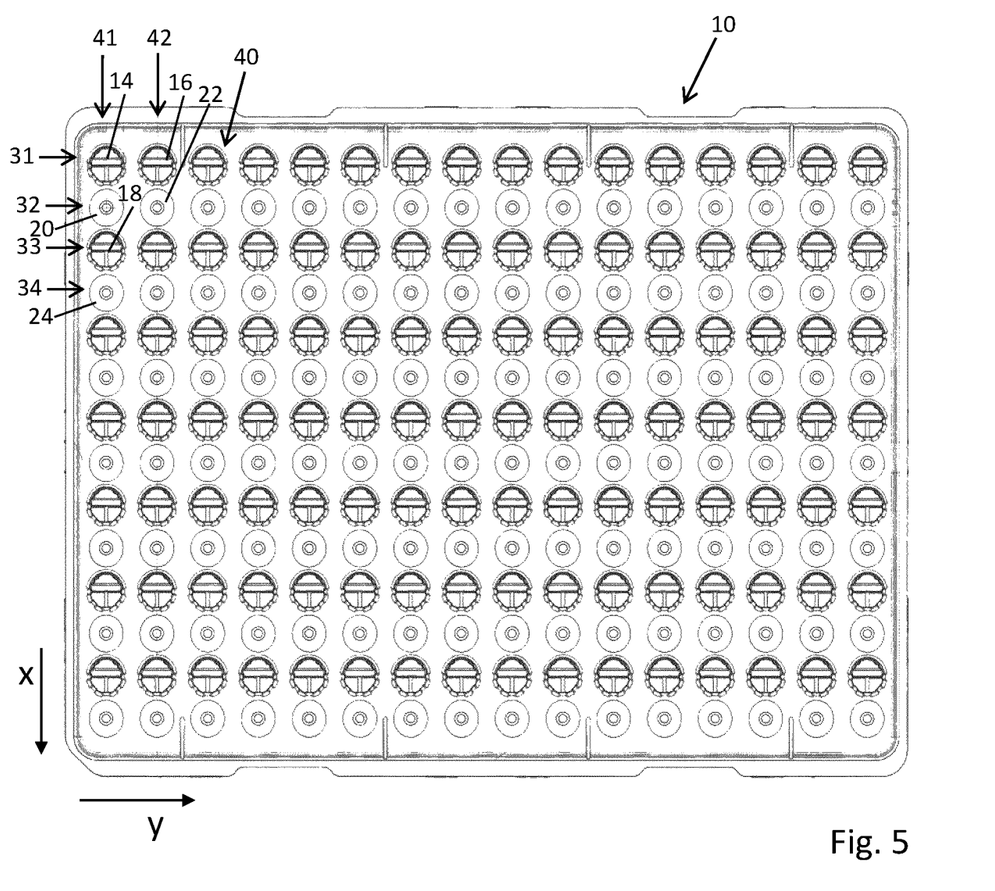
FIG. 5 is a top view of the workpiece carrier of FIG. 1.
Figure 6:
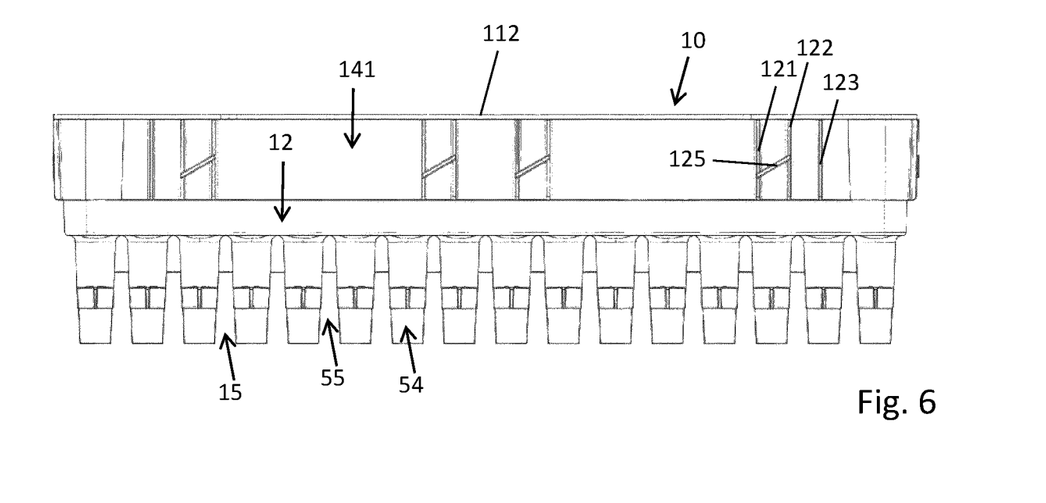
FIG. 6 is another longitudinal side view of the workpiece carrier of FIG. 1.

As shown in FIGS. 1 and 5 the bottom area 12 comprises a two-dimensional array 40 of cavities 14, 16, 18. The cavities 14, 16, 18 are arranged in a regular and equidistant order. The cavities 14, 16 belong to a first row 31 of cavities extending along a second direction (Y). Towards the other direction, hence the first direction (X) co-planar with the bottom area 12 there is provided an alternating arrangement of cavities 14, 18 and depressions 20, 24.

As illustrated in FIG. 5 there is provided a first row 32 of depressions 20, 22. The depressions 20, 22 of the first row of depressions 32 are arranged and aligned along the second direction (Y). Along the first direction (X) there is an alternating arrangement of cavities 31, 33 and depressions 20, 22.

The depressions 20, 22, 24 are located between the cavities 14, 18 as seen along the first direction (X). Along the second direction (Y) there are provided non-interrupted longitudinal rows of cavities 14, 16 and depressions 20, 22. Along the first direction (X) there's provided a first column 41 of an alternating arrangement of cavities 14, 18 and depressions 20, 22. Next to the first column 41 and offset from the first column 41 along the second direction (Y) there is provided a second column 42 of an alternating arrangement of cavities 16 and depressions 22 and so on.

Figure 2:
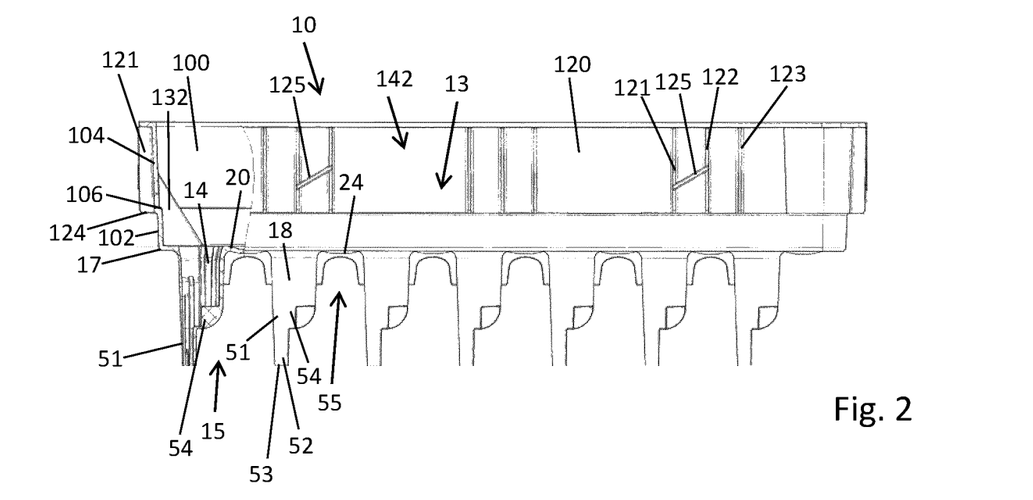
FIG. 2 is a partial cross-sectional side view of the workpiece carrier.

As illustrated, the depressions 20, 22, 24 are of circular shape. As shown in FIG. 2 the depressions 20, 22, 24 comprise a concave shaped cross-section. The recess formed by the depressions 20, 22, 24 is particularly adapted to provide a stable and self-centering support for the longitudinal end 52 of protuberances 54 of a second workpiece carrier 10' stacked on top of a first workpiece carrier 10. The concave shape of the depressions 20, 22, 24 helps to provide a self-centering and a respective alignment of first and second workpiece carriers 10, 10' stacked on top of each other with regards to the first and second directions (X, Y).

Figure 8:
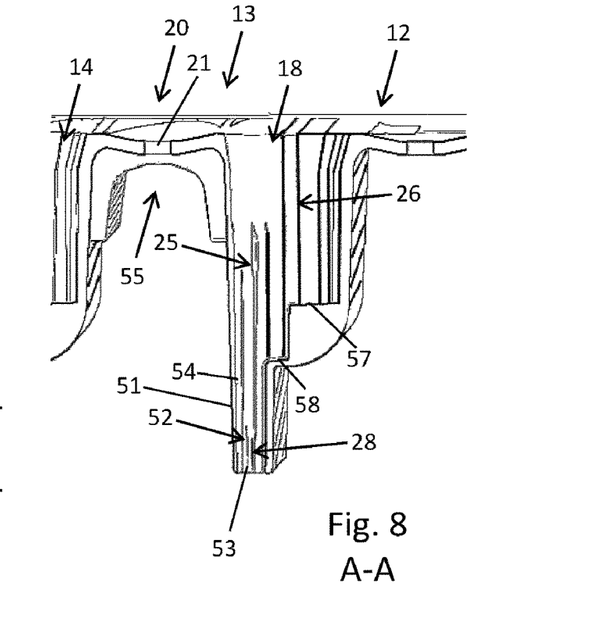
FIG. 8 is a cross-section A-A according to FIG. 7.
Figure 9:
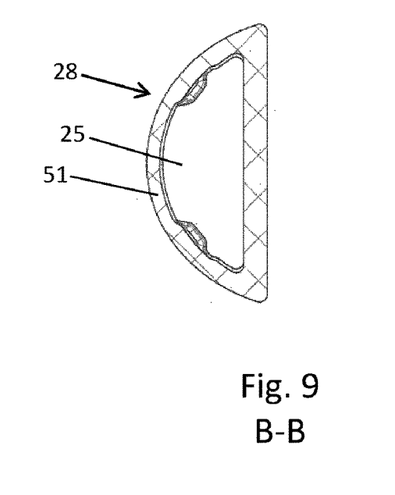
FIG. 9 is a cross-section of B-B according to FIG. 8.
Figure 10:
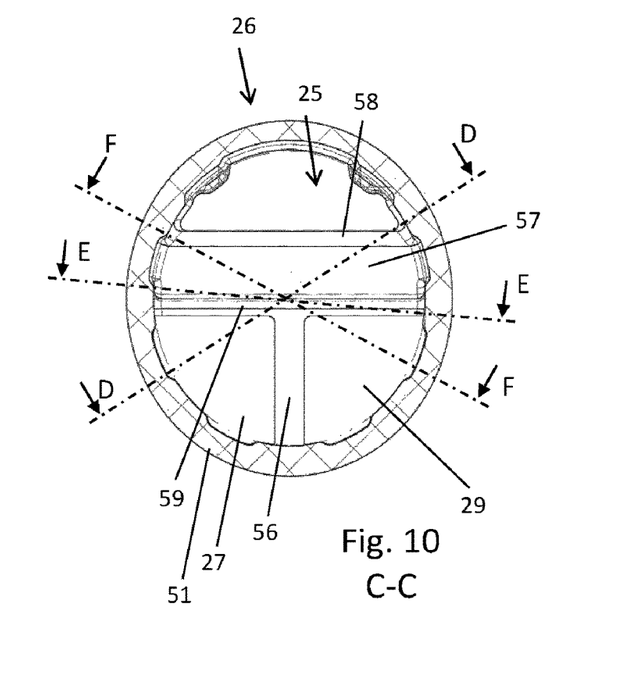
FIG. 10 is a cross-section along C-C according to FIG. 7.
Figure 11:
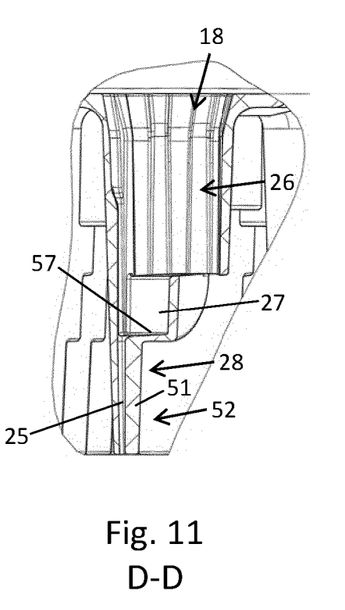
FIG. 11 is a cross-section along D-D according to FIG. 10.
Figure 12:
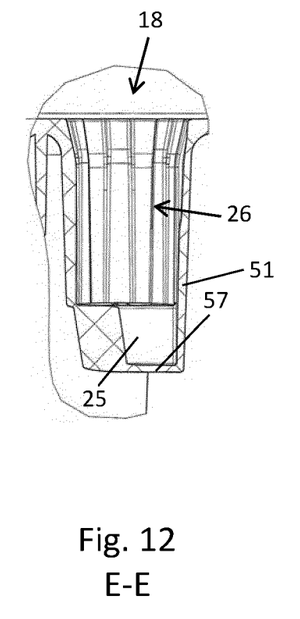
FIG. 12 is a cross-section along E-E according to FIG. 10.
Figure 13:
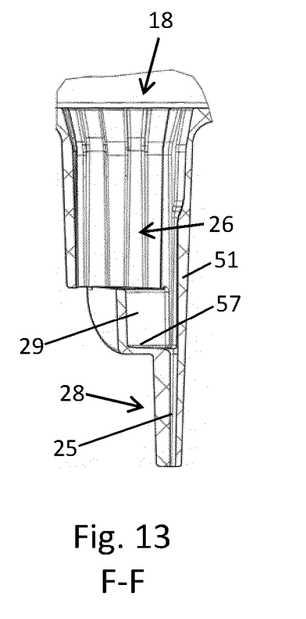
FIG. 13 is a cross-section along F-F according to FIG. 10.

As further illustrated in FIG. 8 the depressions 20, 22, 24 comprise a hole 21 extending through the bottom area 12. With the presently illustrated example, the hole 21 is located in a radial central portion of the concave shaped depressions 20, 22, 24. This way, the hole 21 or aperture extending through the body 11 of the workpiece carrier 10 provides and enables drainage of a liquid cleaning agent, e.g. water.

With typical examples, the body 11 is a one-piece injection molded plastic body. It is of excellent dimensional stability and can be used multiple times for transporting and/or storing components of a drug delivery device.

The longitudinal end 52 of the protuberances 54 protruding downwardly from the bottom side 15 of the bottom area 12 or the body 11 comprises an aperture 53. Hence, the longitudinal end 52 of the protuberances 54 is open and non-sealed. Even though the cavities 14, 16, 18 seem to provide a pocket hole they have an open distal end. Such an open end or aperture 53 is of particular benefit for cleaning of the workpiece carrier 10, e.g. with a cleaning agent, such as water and/or a detergent.

The aperture 53 at the longitudinal end 52 provides a residue-free draining of a liquid cleaning agent. Moreover, the open longitudinal end 52 of the protuberances 54 and/or of the respective cavities 14, 16, 18 provides and enables an improved drying of the workpiece carrier 10 in the process of workpiece carrier cleaning with a liquid cleaning agent.

Typically, the longitudinal end of the protuberances 54 are void of an end face. Hence, the sidewall 51 of the protuberances 54 is void of an end face. In this way, a residue-free draining of a liquid cleaning agent can be easily provided. This enables use of the workpiece carrier 10 in an environment classified as predefined clean room class.

The open longitudinal end of the protuberances are particularly provided by way of injection molding. For providing the open longitudinal end of the protuberances there is no elaborate post-processing necessary. The workpiece carrier 10 can be provided by single shot or by a multi-component injection molding process.

Typically, the depressions 20, 24 are located midway between adjacently located cavities 14, 18. In particular, the depression 20 is located midway between the cavities 14, 18. Interstices 55 on the bottom side 15 of the bottom area 12 located between adjacently located protuberances 54 of a second workpiece 10' carrier may become aligned with the cavities 14, 16, 18 of the first workpiece carrier 10 and may therefore provide room for an upright orientation and accommodation of elongated or longitudinally shaped components 60 of a drug delivery device 1.

As illustrated in FIG. 5 the workpiece carrier 10 forms a transport or storage tray for components 60 of drug delivery devices 1. The tray or workpiece carrier 10 comprises a mirror symmetry with a symmetry axis extending parallel to the first direction (X) and located midway across the workpiece carrier 10 as seen along the second direction (Y).

The workpiece carrier 10 comprises a rectangular structure. The planar-shaped bottom area 12 is of rectangular shape and adjoins an upwardly protruding side wall 10 protruding from the upper side 13 of the planar-shaped bottom area 12. The sidewall 100 encloses the entirety of the bottom area 12. The sidewall 100 forms a rectangular frame 101 that contributes to the stability and stiffness of the workpiece carrier 10. The sidewall 100 comprises an inside surface 130 and an outside surface 120. The sidewall 100 further comprises a first sidewall portion 140 and an oppositely located second sidewall portion 141. There is further provided a third sidewall portion 142 and a fourth sidewall portion 143 located opposite to the third sidewall portion 142.

The first and the second oppositely located sidewall portions 140, 141 are substantially of the same dimensions. The third and the fourth side wall portions 142, 143 also match in size and geometry. There are further provided numerous corner sections 135 by way of which the first sidewall portion 140 adjoins the third sidewall portion 142, the third sidewall portion 142 adjoins the second sidewall portion 141 and the second sidewall portion 141 adjoins the fourth sidewall portion 143, respectively.

The respective sidewall portions 140, 141, 142, 143 form a closed and non-interrupted sidewall and hence a circumferential frame of the workpiece carrier 10. The sidewall 100 comprises an inside surface 130 and an oppositely located outside surface 120.

On the inside surface 120, the sidewall 110 comprises a lower sidewall section 102 and an upper sidewall section 104. The lower sidewall section 102 adjoins the upper side 13 of the bottom area 12 and the upper sidewall section 104 adjoins the lower sidewall section 102. Between the lower sidewall section 102 and the upper side wall section 104 there is provided a stepped section 106. The stepped section 106 provides a well-defined abutment for a nested arrangement of workpiece carriers 10, 10' stacked on top of each other.

Figure 3:
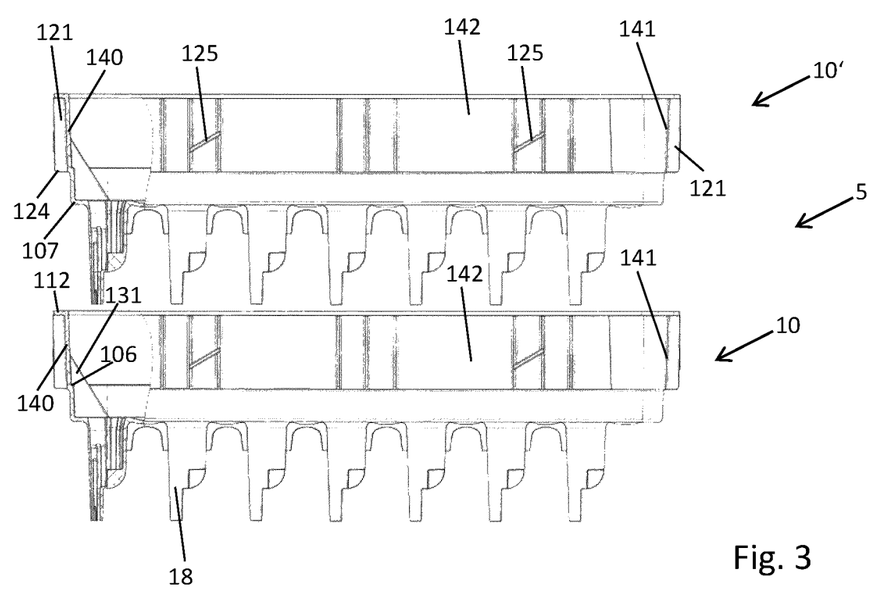
FIG. 3 shows a workpiece carrier assembly with first and second workpiece carriers in a first configuration.

As indicated in FIG. 3 and when a second workpiece carrier 10' is arranged above or on top of a first workpiece carrier 10 in an identical orientation and hence in a first configuration the outer edge section 17 of the bottom area 12 of the second workpiece carrier 10' is vertically aligned with the inwardly extending step section 106 of the first workpiece carrier 10. In this configuration as illustrated in FIG. 3 the first and second workpiece carriers 10, 10' can be arranged in a nested or convoluted manner such that the protuberances 54 of the second workpiece carrier 10' dive into or enter the correspondingly aligned cavities 14, 16, 18 of the first workpiece carrier 10. An end configuration is reached, when an outer corner section 17 of the second workpiece carrier 10' gets in vertical abutment with the inside protrusion of the stepped section 106 of the first workpiece carrier 10.

Of course, in the nested configuration, which is indicated in FIG. 3, the outside surface 120 of the sidewall 100 of the second workpiece carrier 10' gets in alignment or even engages with the inside surface 130 of the first workpiece carrier 10.

As further illustrated in FIG. 1 there are provided numerous struts 131, 132, 133 extending inwardly from the inside surface 130 of the sidewall 100 and extending upwardly from the upper side 13 of the planar-shaped bottom area 12. The struts 131, 132, 133 provide a further mechanical stabilization of the sidewall 100. They further serve to stiffen the body 11 of the workpiece carrier 10. The struts 131, 132, 133 particularly stabilize the sidewall 100 during the process of cooling of the injection molded body 11 and counteract the generation of sink marks in the region of the sidewall 100.

As illustrated in the partial cross-section of FIG. 2 the strut 132 provides a beveled edge or an inclined protrusion from the bottom area 12 and the inside surface 130 of the sidewall. In a nested orientation of first and second workpiece carriers 10, 10', especially in a first configuration of at least two workpiece carriers 10, 10' stacked on top of each other, also the struts 131, 132, 133 of a first workpiece carrier 10 may provide an end stop for a nested arrangement of a second workpiece carrier 10' located thereon. The struts 131, 132, 133 of a first workpiece carrier 10 may abut and engage with the outer edge section 17 at the second workpiece carrier 10' when stacked thereon in the first configuration.

Typically, there are provided numerous struts 131, 132, 133 along the first sidewall portion 140 and along the second sidewall portion 141 in this way, oppositely located corner sections 17 of the second workpiece carrier 10' can engage with the beveled edges provided by the struts 131, 132, 133.

As further illustrated in FIG. 1 the sidewall 100 forms a circumferential frame 101 featuring an upper edge 110 that faces away from the upper side 13 of the bottom area 12. The upper edge 110 of the frame 101 and/or of the sidewall 100 is provided with an outwardly protruding flange 112. The outwardly protruding flange 112 provides and enables an easy gripping and lifting of the workpiece carrier 10 from above. The flange 112 further contributes to the stiffening and mechanical stability of the sidewall 100.

As further illustrated in FIG. 1, the flange 112 comprises numerous gripping recesses 114 at least in the region of the first sidewall portion 140 and the second sidewall portion 141. The gripping recesses provide and enable a lifting of workpiece carriers from above even when identical workpiece carriers should be positioned next to each other in such a way that the outwardly extending flanges of first and a second workpiece carriers mutually touch.

The outside surface 120 of the sidewall 100 is further provided with numerous elongated ribs 121, 122, 123 as shown in FIG. 1. The outwardly protruding extension of these rips 121, 122, 123 substantially equals the respective outwardly directed extension of the flange 112. An upper end of the elongated ribs 121, 122, 123 may adjoin a lower side of the flange 112. In this way, the flange 112 and the sidewall 110 may experience a further stabilization and mechanical stiffening.

The elongated ribs 121, 122, 123 are of rather straight shape, which is beneficial for a demolding when the workpiece carrier 10 or tray is manufactured as a one-piece injection molded plastic body 11.

Figure 4:
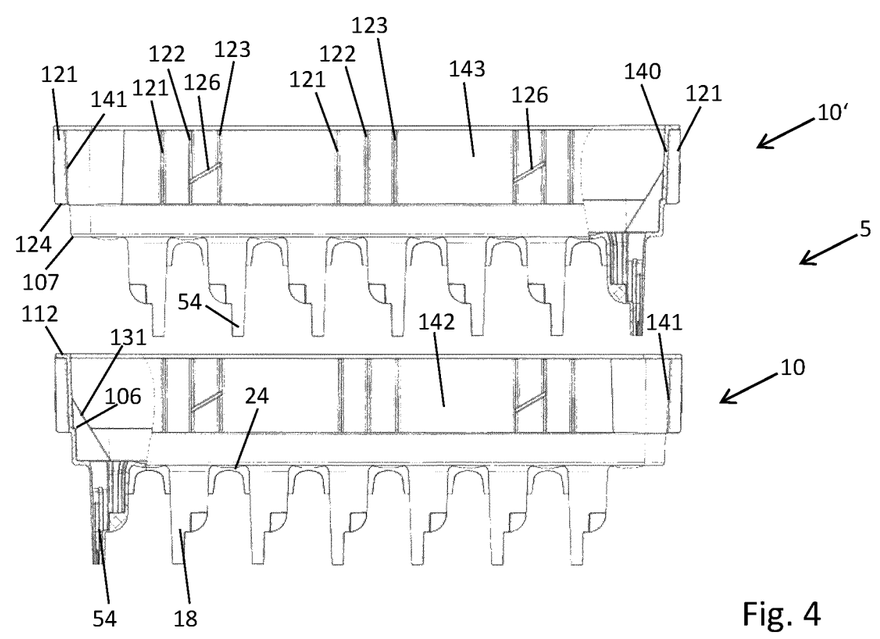
FIG. 4 shows the workpiece carrier assembly of FIG. 3 with the second workpiece carrier in the second configuration.

As further illustrated in FIG. 4 the longitudinally extending ribs 121, 122 comprise a lower end 124 forming a stop face or an abutment for a second workpiece carrier 10' when stacked on a first workpiece carrier 10 in the second configuration. Here, the lower end 124 of ribs 121, 122, 124 of the sidewall 110 of a second workpiece carrier 10' facing downwardly and oriented substantially parallel to the bottom area 12 may abut in vertical direction with the outer edge 110 and hence with the outwardly protruding flange 112 of the first workpiece carrier 10, especially when in one of the first or second configurations as illustrated in FIGS. 3 and 4.

The orientation of the second workpiece carrier 10' as illustrated in FIG. 4 has been flipped over or inverted compared to the orientation at shown in FIG. 3. Now the stacking of the second workpiece carrier 10' onto the first workpiece carrier 10 is also possible but the protuberances 54 of the second workpiece carrier 10' do no longer align with the cavities 14, 16, 18 of the first workpiece carrier 10. Rather, the protuberances 54 of the second workpiece carrier 10' align with the depressions 20, 22, 24 of the first workpiece carrier 10 when reaching the second configuration. Here, the protuberances 54 may experience a kind of a self-centering with regards to the first direction (X) and/or with regards to the second direction (Y) due to the concave shaped cross-section of the depressions 20, 22, 24.

As it is further apparent from FIG. 4 also in the second configuration of the workpiece carrier assembly 5 the outside surface 120 of the second workpiece carrier 10' may align or engage with the inside surface 130 of the sidewall 110 of the first workpiece carrier 10. The abutment of the lower end 124 of the elongated ribs 121, 122, 123 of the second workpiece carrier 10' with the flange 112 of the second workpiece carrier 10 may provide further stabilization of a stack of numerous workpiece carriers 10, 10'.

As further illustrated in FIG. 1, there are provided numerous crossbeams 125 protruding outwardly from the outside surface 120 of the sidewall 100. The crossbeams 125 are of elongated and straight shape and extend at a predefined first angle on the outside surface 120. The first angle is a non-zero angle with regard to the elongation of the longitudinally extending ribs 121, 122, 123 and/or with regards to the elongation of the flange 112. The crossbeams 125 comprise an outwardly extending protrusion that is substantially equal to the outwardly extending protrusion as provided by the longitudinally extending ribs 121, 122, 123.

In the example of FIG. 1 the crossbeam 125 extends at a predefined angle, e.g. at about 45° with regards to the elongation of the longitudinally extending ribs 121, 122, 123. The crossbeams 125 extends between the ribs 122 and the ribs 123. It may also extend between the ribs 121 and the ribs 122. The crossbeam 125 provides a further mechanical stabilization and stiffening of the sidewall 100. Moreover, the crossbeam 125 prevents a lateral intrusion or a lateral partial intersection of first and second workpiece carriers when arranged next to each other.

As it is apparent from the illustration of FIGS. 1 and 4, the third sidewall portion 142 is provided with two crossbeams 125 of a first type. The crossbeams 125 are located at a dedicated position at the third sidewall portion 142. Directly opposite the third sidewall portion 142 there is provided the fourth sidewall portion 143. The fourth sidewall portion 143 comprises two crossbeams 126 of a second type. In the second configuration of the workpiece carrier assembly 5 as shown in FIG. 4 the crossbeams 125 of the first type provided at the third sidewall portion 142 are somewhat similar in position and shape compared to the crossbeams 126 of the oppositely located second sidewall portion 143.

Presumed that the first and second workpiece carriers 10, 10' are arranged next to each other in the same orientation, the crossbeams 125 of the first workpiece carrier 10 will be located directly opposite and adjacent to the crossbeams 126 of the second workpiece carrier 10'. Then and when facing towards each other the crossbeams 125, 126 form an X-shaped structure between first and second workpiece carriers 10, 10'. The crossbeams 125, 126 of first and second workpiece carriers 10, 10' even mutually abut even when there should be an alignment mismatch with regards to the first direction or second direction (X, Y). With the crossbeams 125, 126 a mutual intrusion or at least partial overlapping of the sidewall 100 of the first workpiece carrier 10 with the sidewall 100 of the second workpiece carrier 10' can be effectively prevented.

Generally it is sufficient, when only one sidewall section 142 is provided with only one type of crossbeams 125 and when the oppositely located sidewall portion 143 is provided with a longitudinally extending rib 121, 122, 123 that overlaps with the crossbeam 125 when the first and the second workpiece carriers are arranged next to each other such that the crossbeam 125 faces the respective rib(s) 121, 122, 123.

Figure 7:
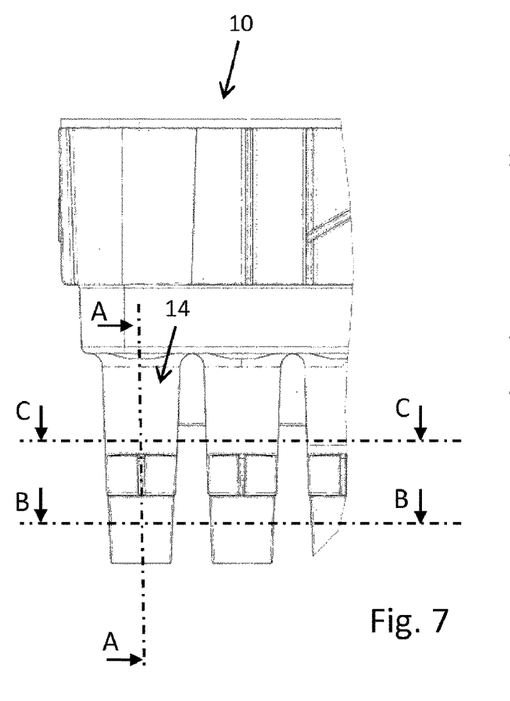
FIG. 7 is an enlarged portion of the side view of FIG. 6.

In the further illustration of FIGS. 7-13 the particular shape and geometry of a cavity 14 is further illustrated in detail. As shown in FIG. 7 the elongated cavity 14 comprises an upper portion 26 with a somewhat circular-shaped cross-section and a bottom portion 28. As shown in the cross-section of FIG. 9 the bottom portion 28 is of somewhat semicircular shape. It comprises a sidewall 51 extending into a respective sidewall of the upper portion 26. As shown in the cross-section A-A of FIG. 8 the lower portion 28 is a longitudinal extension of the upper portion 26.

The lower portion 28 is a rather straight extension of a first compartment 25 extending straight through the upper portion 26 and into the lower portion 28. The compartment 25 is separated from further compartments 27, 29 by a separation wall 56, 59. The separation wall 59 divides the upper part 26 of the cavity 14 into an upper and a lower half. The lower half is separated by a further separation wall 56. The two separation walls 56, 59 may be regarded as portions of a single T-shaped separation wall.

The separation wall 59 is terminated in a downward direction by a bottom section 57, 58. The bottom section 57 is an upper plateau and the bottom section 58 is a lower plateau is located in the first compartment 25 and forming a stepped down portion towards the lower part 28 of the cavity 14.

The separation wall 56 divides the upper part 26 of the cavity 14 into a second compartment 27 and a third compartment 29. Both compartments 27, 29 feature a common depth and terminate in downward direction at the bottom section 57.

Typically, the separation walls 56, 59 extend towards the upper opening of the cavity 14. The particular shape of the lower port part 28 provide an accommodation space for a dedicated component 60 of the drug delivery device 1. The component 60 comprises a tubular shaped sleeve portion 61 and a semicircular shaped longitudinal extension 62. The longitudinal extension 62 is particularly dedicated for insertion into the semicircular shaped lower part 28 of the cavity 14. The separation wall 56 effectively prevents a misaligned insertion of the device component 60 and/or of its longitudinal protrusion 61 into one of the second and third compartments 27, 29. Moreover, the first compartment 25 is complementary shaped to the shape and geometry of the protrusion 62 of the device component 60. It allows and supports insertion of the device component 60 in one predefined orientation.

LIST OF REFERENCE NUMBERS 1 drug delivery device
5 workpiece carrier assembly
10 workpiece carrier
11 body
12 bottom area
13 upper side
14 cavity 15 bottom side
16 cavity
17 corner section
18 cavity
20 depression
22 depression
24 depression
25 compartment
26 upper part
27 compartment
28 lower part
29 compartment
31 row of cavities
32 row of depressions
33 row of cavities
34 row of depressions
40 array
41 column
42 column
51 sidewall
52 longitudinal end
53 aperture
54 protuberance
55 interstice
56 separation wall
57 bottom section
58 bottom section
59 separation wall
60 device component
61 sleeve
62 protrusion
100 sidewall
101 frame
102 lower sidewall section
104 upper sidewall section
106 step section
110 upper edge
112 flange
114 gripping recess
120 outside surface
121 rib
122 rib
123 rib
124 lower end
125 crossbeam
126 crossbeam
130 inside surface
131 strut
132 strut
133 strut
135 corner section
140 sidewall portion
141 sidewall portion
142 sidewall portion
143 sidewall portion

The invention claimed is:

1. A workpiece carrier for components of a drug delivery device, the workpiece carrier comprising:
    a body comprising a planar-shaped bottom area, the planar-shaped bottom area comprising an upper side and a bottom side opposite to the upper side,
    the bottom area comprising a number of longitudinally extending hollow protuberances protruding from the bottom side and forming longitudinally extending cavities in the upper side,
    wherein a longitudinal end of at least one of the protuberances or cavities facing away from the bottom side comprises an aperture,
    wherein the protuberances are inversely shaped to the cavities and wherein an outer shape or cross-section of the protuberances directly matches and corresponds to an inner shape or cross-section of the cavities.

2. The workpiece carrier according to claim 1, wherein the body is a one-piece injection molded plastic body.

3. The workpiece carrier according to claim 1, wherein the body comprises a number of depressions in the upper side of the bottom area, wherein the depressions and the cavities are adjacently arranged in an alternating order along a first direction.

4. The workpiece carrier according to claim 3, wherein the body comprises at least one of a row of cavities extending along a second direction and a row of depressions extending along the second direction.

5. The workpiece carrier according to claim 3, wherein the depressions comprise a concave shaped cross-section.

6. The workpiece carrier according to claim 1, wherein the cavities are configured to receive at least one longitudinally extended component of a drug delivery device such that the at least one longitudinally extended component is positioned upright within the cavities.

7. The workpiece carrier according to claim 1, wherein the cavities are configured to receive protuberances of another workpiece carrier vertically from above the workpiece carrier.

8. The workpiece carrier according to claim 1, wherein the body comprises a sidewall protruding from the upper side of the planar-shaped bottom area and surrounding the planar-shaped bottom area.

9. The workpiece carrier according to claim 8, further comprising at least one strut extending inwardly from an inside surface of the sidewall and extending upwardly from the upper side of the planar-shaped bottom area.

10. The workpiece carrier according to claim 9, wherein the at least one strut provides a beveled section in a corner of the sidewall and the upper side of the bottom area.

11. The workpiece carrier according to claim 8, wherein the sidewall comprises at least one longitudinally extending rib protruding from an outside surface of the sidewall.

12. The workpiece carrier according to claim 11, wherein the at least one longitudinally extending rib comprises a lower end located at a predefined distance from the bottom area.

13. The workpiece carrier according to claim 8, wherein the sidewall comprises a first crossbeam extending along a first angle on an outside surface of a first sidewall portion of the sidewall and protruding outwardly from the first sidewall portion.

14. The workpiece carrier according to claim 13, wherein the sidewall comprises at least one of a longitudinally extending rib and a second crossbeam extending along a second angle on an outside surface of a second sidewall portion of the sidewall opposite to the first sidewall portion and protruding outwardly from the second sidewall portion.

15. The workpiece carrier according to claim 14, wherein the second angle at which the second crossbeam or the longitudinally extending rib extends is different from the first angle at which the first crossbeam extends.

16. The workpiece carrier according to claim 8, wherein the sidewall comprises a lower sidewall section and an upper side wall section, the lower sidewall section adjoining the upper side of the bottom area and the upper sidewall section adjoining the lower side wall section via a step section located between the lower side wall section and the upper sidewall section.

17. The workpiece carrier according to claim 1, wherein the cavities comprise an upper portion and a lower portion, the upper portion adjoining the bottom area and the lower portion adjoining the longitudinal end, wherein an inner diameter of the lower portion is smaller than an inner diameter of the upper portion.

18. The workpiece carrier according to claim 17, wherein the upper portion comprises a longitudinally extending separation wall dividing the upper portion at least into a first compartment and a second compartment.

19. An assembly comprising:
   a plurality of longitudinally extending components of drug delivery devices; and
   at least two workpiece carriers, each workpiece carrier comprising a body having a planar-shaped bottom area having an upper side and a bottom side opposite to the upper side, the bottom area comprising (i) a number of longitudinally extending hollow protuberances protruding from the bottom side and forming a row of longitudinally extending cavities that extend along a first direction, and (ii) a row of depressions formed in the upper side that extend along the first direction, the depressions and the cavities being adjacently arranged in an alternating order along a second direction, a longitudinal end of at least one of the protuberances or cavities facing away from the bottom side comprising an aperture,
   wherein the protuberances are inversely shaped to the cavities and wherein an outer shape or cross-section of the protuberances directly matches and corresponds to an inner shape or cross-section of the cavities.

20. The assembly of claim 19, wherein the cavities of each workpiece carrier are shaped to receive the longitudinally extending components of the drug delivery devices such that the at least two workpiece carriers are stackable in an alternating manner when the longitudinally extending components are received in the cavities.

21. A workpiece carrier for components of a drug delivery device, the workpiece carrier comprising:
   a body comprising a planar-shaped bottom area, the planar-shaped bottom area comprising an upper side and a bottom side opposite to the upper side,
   the bottom area comprising a number of longitudinally extending hollow protuberances protruding from the bottom side and forming longitudinally extending cavities in the upper side,
   wherein a longitudinal end of at least one of the protuberances or cavities facing away from the bottom side comprises an aperture; and
   wherein the cavities comprise an upper portion and a lower portion, the upper portion adjoining the bottom area and the lower portion adjoining the longitudinal end, wherein an inner diameter of the lower portion is smaller than an inner diameter of the upper portion.

22. The workpiece carrier according to claim 21, wherein the upper portion comprises a longitudinally extending separation wall dividing the upper portion at least into a first compartment and a second compartment.

\* \* \* \* \*